(12) United States Patent
Mäntylä et al.

(10) Patent No.: US 7,462,701 B2
(45) Date of Patent: Dec. 9, 2008

(54) NON-DENATURING PROCESS TO PURIFY RECOMBINANT PROTEINS FROM PLANTS

(75) Inventors: Einar Mäntylä, Reykjavik (IS); Bjorn Larus Orvar, Kopavogur (IS)

(73) Assignee: Orf Liftaekni HF., Reykjavik (IS)

( * ) Notice: Subject to any disclaimer, the term of this patent is extended or adjusted under 35 U.S.C. 154(b) by 109 days.

(21) Appl. No.: 10/569,792

(22) PCT Filed: Aug. 27, 2004

(86) PCT No.: PCT/IS2004/000010

§ 371 (c)(1),
(2), (4) Date: Aug. 3, 2006

(87) PCT Pub. No.: WO2005/021762

PCT Pub. Date: Mar. 10, 2005

(65) Prior Publication Data

US 2007/0169223 A1 Jul. 19, 2007

Related U.S. Application Data

(60) Provisional application No. 60/497,935, filed on Aug. 27, 2003.

(30) Foreign Application Priority Data

Aug. 27, 2003 (IS) .......................................... 6929

(51) Int. Cl.
*A23J 1/00* (2006.01)

(52) U.S. Cl. ..................................... 530/412; 435/69.7

(58) Field of Classification Search ................ 530/412; 435/69.7, 69.1
See application file for complete search history.

(56) References Cited

U.S. PATENT DOCUMENTS

| 6,048,715 A | 4/2000 | Haynes et al. |
| 6,331,416 B1 * | 12/2001 | Shani et al. ................ 435/69.7 |
| 2002/0164718 A1 | 11/2002 | Tchaga et al. |

FOREIGN PATENT DOCUMENTS

| WO | WO-00/77174 A | 12/2000 |
| WO | WO-02/05922 A | 1/2002 |

OTHER PUBLICATIONS

Boraston, Alisdair B et al., Biochemistry, vol. 40, No. 21, May 29, 2001, pp. 6240-6247.
Boraston, Alisdair B et al., Protein Expression and Purification, vol. 21, No. 3, Apr. 2001, pp. 417-423.
Reeves, R.A. et al., Applied and Environmental Microbiology, Apr. 2000, vol. 66, No. 4, Apr. 2000, pp. 1532-1537.
Chhabra, S.R. et al., FEBS letters, Elsevier Science Publishers, vol. 531, No. 2, Nov. 6, 2002, pp. 375-380.

* cited by examiner

*Primary Examiner*—Tekchand Saidha
(74) *Attorney, Agent, or Firm*—Birch, Stewart, Kolasch & Birch, LLP

(57) ABSTRACT

The present invention relates to improved methods for protein purification of high-value heterologous proteins produced in plants, plant derived tissue or plant cells. The invention aims to reduce the cost and improve the quality of downstream processing of heterologous proteins produced in plants.

22 Claims, 3 Drawing Sheets

SEQUENCE LISTING

<160> NUMBER OF SEQ ID NOS: 3

<210> SEQ ID NO 1
<211> LENGTH: 564
<212> TYPE: DNA
<213> ORGANISM: Thermotoga maritima

<400> SEQUENCE: 1

```
gtggccaccg ccaagtacgg caccccagtg atcgacgggg agatcgacga gatctggaac      60
accaccgagg agatcgagac caaggccgtg gccgtgggga gcctcgacaa gaacgccacc     120
gccaaggtgc gcgtgctctg ggacgagaac tacctctacg tgctcgccat cgtgaaggac     180
ccagtgctca acaaggacaa cagcaacccc tgggagcaag acagcgtgga gatcttcatc     240
gacgagaaca accacaagac cggctactac gaggacgacg acgcccaatt ccgcgtgaac     300
tacatgaaca gcaaaacctt cgggaccggc gggagcccag cccgcttcaa gaccgccgtg     360
aagctcatcg aggggggcta catcgtggag ccgccatca agtggaagac catcaagcca     420
accccaaaca ccgtgatcgg cttcaacatc caagtgaacg acgccaacga aaggggcaa      480
cgcgtgggga tcatcagctg gagcgaccca accaacaaca gctggcgcga cccaagcaag     540
ttcgggaacc tccgcctcat caag                                            564
```

<210> SEQ ID NO 2
<211> LENGTH: 705
<212> TYPE: DNA
<213> ORGANISM: Bos taurus

<400> SEQUENCE: 2

```
atcgtcggcg ggagcgattc cagggagggc gcatggccat gggtcgtggc actctacttc      60
gatgatcaac aagtctgcgg ggcatccctg gtgagcaggg attggctcgt gtccgcagca     120
cattgcgtgt acggcaggaa catggagcca tccaagtgga aggcagtgct cggcctgcat     180
atggcatcca acctcacctc cccacaaata gagaccaggt tgatcgatca aatcgtcata     240
aacccacatt acaacaagcg gaggaagaac aacgacatcg caatgatgca tctcgagatg     300
aaggtgaact acaccgatta catacaacca atctgcttgc cagaggagaa ccaagtgttc     360
ccaccaggga ggatctgctc catcgcaggc tggggcgcac tcatatacca agggtccacc     420
gcagatgtac tgcaagaggc agacgtgcca ctcctctcca acgagaagtg ccaacaacaa     480
atgccagagt acaacatcac cgagaacatg gtgtgcgcag gctacgaggc aggcggggta     540
gattcctgcc aaggcgattc cggcgggcca ctcatgtgcc aagagaacaa caggtggctc     600
ctggcaggcg tgacctcctt cggctaccaa tgcgcactcc caaaccggcc aggggtgtac     660
gcacgggtgc caaggttcac cgagtggata caaagcttcc tccat                    705
```

<210> SEQ ID NO 3
<211> LENGTH: 564
<212> TYPE: PRT
<213> ORGANISM: Aborophila torqueola

<400> SEQUENCE: 3

```
Gly Thr Gly Gly Cys Cys Ala Cys Cys Gly Cys Cys Ala Ala Gly Thr
1               5                   10                  15

Ala Cys Gly Gly Cys Ala Cys Cys Cys Cys Ala Gly Thr Gly Ala Thr
                20                  25                  30

Cys Gly Ala Cys Gly Gly Gly Gly Ala Gly Ala Thr Cys Gly Ala Cys
            35                  40                  45
```

-continued

```
Gly Ala Gly Ala Thr Cys Thr Gly Gly Ala Ala Cys Ala Cys Cys Ala
    50                  55                  60

Cys Cys Gly Ala Gly Gly Ala Gly Ala Thr Cys Gly Ala Gly Ala Cys
65                  70                  75                  80

Cys Ala Ala Gly Gly Cys Cys Gly Thr Gly Gly Cys Cys Gly Thr Gly
                85                  90                  95

Gly Gly Gly Ala Gly Cys Cys Thr Cys Gly Ala Cys Ala Ala Gly Ala
            100                 105                 110

Ala Cys Gly Cys Cys Ala Cys Cys Gly Cys Cys Ala Ala Gly Gly Thr
        115                 120                 125

Gly Cys Gly Cys Gly Thr Gly Cys Thr Cys Thr Gly Gly Gly Ala Cys
    130                 135                 140

Gly Ala Gly Ala Ala Cys Thr Ala Cys Cys Thr Cys Thr Ala Cys Gly
145                 150                 155                 160

Thr Gly Cys Thr Cys Gly Cys Cys Ala Thr Cys Gly Thr Gly Ala Ala
                165                 170                 175

Gly Gly Ala Cys Cys Cys Ala Gly Thr Gly Cys Thr Cys Ala Ala Cys
            180                 185                 190

Ala Ala Gly Gly Ala Cys Ala Ala Cys Ala Gly Cys Ala Ala Cys Cys
        195                 200                 205

Cys Cys Thr Gly Gly Gly Ala Gly Cys Ala Ala Gly Ala Cys Ala Gly
    210                 215                 220

Cys Gly Thr Gly Gly Ala Gly Ala Thr Cys Thr Thr Cys Ala Thr Cys
225                 230                 235                 240

Gly Ala Cys Gly Ala Gly Ala Ala Cys Ala Ala Cys Cys Ala Cys Ala
                245                 250                 255

Ala Gly Ala Cys Cys Gly Gly Cys Thr Ala Cys Thr Ala Cys Gly Ala
            260                 265                 270

Gly Gly Ala Cys Gly Ala Cys Gly Ala Cys Gly Cys Cys Cys Ala Ala
        275                 280                 285

Thr Thr Cys Cys Gly Cys Gly Thr Gly Ala Ala Cys Thr Ala Cys Ala
    290                 295                 300

Thr Gly Ala Ala Cys Gly Ala Gly Cys Ala Ala Ala Cys Cys Thr Thr
305                 310                 315                 320

Cys Gly Gly Gly Ala Cys Cys Gly Gly Cys Gly Gly Gly Ala Gly Cys
                325                 330                 335

Cys Cys Ala Gly Cys Cys Cys Gly Cys Thr Thr Cys Ala Ala Gly Ala
            340                 345                 350

Cys Cys Gly Cys Cys Gly Thr Gly Ala Ala Gly Cys Thr Cys Ala Thr
        355                 360                 365

Cys Gly Ala Gly Gly Gly Gly Gly Gly Cys Thr Ala Cys Ala Thr Cys
    370                 375                 380

Gly Thr Gly Gly Ala Gly Gly Cys Cys Gly Cys Cys Ala Thr Cys Ala
385                 390                 395                 400

Ala Gly Thr Gly Gly Ala Ala Gly Ala Cys Cys Ala Thr Cys Ala Ala
                405                 410                 415

Gly Cys Cys Ala Ala Cys Cys Cys Cys Ala Ala Ala Cys Ala Cys Cys
            420                 425                 430

Gly Thr Gly Ala Thr Cys Gly Gly Cys Thr Thr Cys Ala Ala Cys Ala
        435                 440                 445

Thr Cys Cys Ala Ala Gly Thr Gly Ala Ala Cys Gly Ala Cys Gly Cys
    450                 455                 460
```

-continued

```
Cys Ala Ala Cys Gly Ala Gly Ala Ala Gly Gly Gly Gly Cys Ala Ala
465             470             475             480
Cys Gly Cys Gly Thr Gly Gly Gly Ala Thr Cys Ala Thr Cys Ala
            485             490             495
Gly Cys Thr Gly Gly Ala Gly Cys Gly Ala Cys Cys Cys Ala Ala Cys
        500             505             510
Cys Ala Ala Cys Ala Ala Cys Ala Gly Cys Thr Gly Gly Cys Gly Cys
        515             520             525
Gly Ala Cys Cys Cys Ala Ala Gly Cys Ala Ala Gly Thr Thr Cys Gly
    530             535             540
Gly Gly Ala Ala Cys Cys Thr Cys Cys Gly Cys Cys Thr Cys Ala Thr
545             550             555             560
Cys Ala Ala Gly
```

NON-DENATURING PROCESS TO PURIFY RECOMBINANT PROTEINS FROM PLANTS

FIELD OF THE INVENTION

The present invention is in the area of biochemistry and protein technology and relates to improved methods of isolation and purification of heterologous proteins from transgenic plant material.

BACKGROUND

Protein based biopharmaceuticals show great promise in providing more specific and tissue specific, or cell specific drug treatments against serious diseases (for overview see "Recombinant Protein Drugs" Ed. P. Buckel 2001).

Numerous examples in the prior art and applications have demonstrated the use of microorganisms such as bacteria, and animal cells for the production of such biopharmaceuticals, of which insulin is a notable example.

Many examples in the literature have demonstrated the utilization of transgenic plants or plant cell cultures for expression and manufacturing of high-value heterologous polypeptides or biopharmaceuticals. Such plant-based manufacturing process may be called molecular farming.

Production of valuable proteins can be made more economical by the use of plants as production organisms. The cultivation cost for plants used as host organisms for protein manufacturing can be considerably lower compared to most production systems based on bioreactors, such as prokaryotic production systems, animal cell cultivation and so forth. However, for all of the above production systems, purification of heterologous proteins remains a demanding and costly task. Thus, for plant-based production systems, downstream processing generates most of the production costs in the manufacturing of high-value heterologous proteins.

Protein purification and isolation is a key process in downstream processing of proteins accumulated and produced in a variety of host organisms by the use of gene technology. The purification of proteins from the host organisms can be quite laborious, complex and expensive. A variety of chromatographic strategies are used commercially for separation and purification of proteins of interest from production host organisms. The chromatographic strategies may rely on physicochemical differences between contaminating or endogenous proteins and the heterologous protein of interest, such as in size, solubility, charge, hydrophobicity, and affinity.

Combinations of chromatographic strategies consisting of multiple steps, require several expensive chromatography matrices and the necessary hardware consisting of columns, control units and so forth, and are accompanied by product yield-losses at each step, and consequently, economical losses. In addition to the chromatographic steps involved, downstream processing typically involves multiple filtering and centrifugation steps. As a result, the cost of purification and downstream processing may become prohibitive for the purification of a protein based biotechnological product. As for a number of protein-based products of lesser value, such as industrial proteins, the cost of downstream processing can be inhibitory for their use and marketing, resulting in crude and poorly defined products. For most biotechnology products purification costs are certainly a major proportion of the manufacturing costs.

The cost of specialized chromatography matrices effecting the separation of a protein of interest from contaminants is high as a result of complex coupling chemistry involved in their production. Some common chromatography methods are ion exchange chromatography, hydrophobic interaction chromatography and reversed phase chromatography. Ligands coupled to a matrix may include a variety of diethylaminoethyl- or quaternary aminoethyl groups as anion exchangers and carboxymethyl substituents and sulfonate groups and phosphates as cation exchangers of varying strength (Scopes, 1993), hydrophobic alkyl, phenyl or butyl groups coupled to crosslinked agarose matrices for hydrophobic interaction chromatography (Hydrophobic Interaction Chromatography (HIC) nr. 18-1020-90, Amersham Pharmacia Biotech), or hydrophobic n-alkyl groups as ligands grafted to a porous, insoluble beaded matrices composed of silica or synthetic organic polymers (Reversed phase Chromatography (RPC), Code nr. 18-11134-16, Amersham Pharmacia Biotech) The chemical complexity of these matrices may cause unwanted leaching of ligands and other substances from the matrix during a purification procedure, where necessary preventive measures, monitoring, or the removal of leachates from the protein of interest add to the already high cost of downstream processing.

Affinity chromatography is among the most powerful purification principles as it is based on specific affinity between an agent and a specific ligand, often mimicking a natural protein-ligand interaction. Several different kinds of affinity adsorbents are available, some highly specific for a particular protein, others binding to classes of proteins rather than particular proteins. In many cases affinity chromatography implies the use of an immobilized ligand to an adsorbent that specifically selects out proteins binding to that ligand. The coupling of ligands to affinity adsorbents involves the use of coupling chemistry such as cyanogen bromide-, tosyl-, or vinylsulfone-activation of adsorbents. The ligand coupled to the column matrix may or may not be of proteinaceous origin. Examples of the former are, but not limited to, immobilized protein A or protein G having affinity for ?-globulin, therefore being useful in the purification of antibodies, and lectins with affinity for glycoproteins. As an example of the latter, immobilized glutathione coupled to matrix binds fusion proteins containing a glutathione S-transferase domain. Immobilized metal affinity chromatography (IMAC) is based on immobilization of metal-chelating ligands to a matrix and relies on the formation of weak coordinate bonds between metal ions immobilized on a column and basic groups on proteins, mainly histidine residues. Commercial cloning vectors provide for cloning of a cDNA in frame with a string of histidine residues—a His-tag, that enables the purification of the resultant fusion protein with IMAC. Although widely used for small-scale purification of proteins, IMAC is a non-specific but selective method, as native histidine residues in contaminating proteins can lead to binding in IMAC (Scopes 1993). Several different kinds of tags or binding domains are available in commercial expression vectors resulting in fusion proteins where the tag/binding domain binds the fusion protein to a ligand coupled onto a column matrix.

High specificity of protein binding can be achieved with these matrix-ligand systems. In the cases mentioned above, complex coupling chemistry is involved to immobilize a ligand onto an inert matrix. Consequently, the cost of an affinity matrix can often become inhibitory to industrial scale applications of this powerful technique. Furthermore, as with most other types of chromatography methods, the stability of the coupling of the ligand to the matrix becomes an issue and leaching is of great concern. Heavy metal leaching in IMAC can cause unacceptable and serious contamination in many sensitive purification processes for bioactive proteins, and may inactivate proteins being purified (Scopes 1993).

It is of particular relevance for the present invention that it is not uncommon that the binding affinity of a protein to its ligand is so strong that conditions for elution, to disrupt the ligand-protein binding, require drastic conditions that partly denature the valuable protein being purified. A non-limiting example of this is the elution of antibodies from Protein A-affinity matrix, requiring denaturing at low pH to release the antibody from the column. Including a denaturing step in a protein purification process is undesirable due to the risk of loss of activity of the purified protein, the addition of an extra step for refolding the protein and subsequent activity analysis requirements for the refolded protein product, and the added cost involved.

To enable the use of affinity-based chromatography for large scale purification from plants, it is highly desirable to develop a non-denaturing protein purification process that is simpler and more economic than the current measures commercially available, with less coupling chemistry involved and compatible with the quality requirements of the pharmaceutical industry standards.

Plant-based production of proteins shows great promise for large scale manufacturing of proteins in an economic manner, as has been shown by examples in literature (for overview see Hammond 1999). The cultivation costs involved in molecular farming with plants are considerably lower than with traditional bioreactor-based methods. Whereas upstream events in plant-based production look particularly promising, the downstream processing is facing the same challenges as the rest of the protein production industry.

Polysaccharides and polysaccharide binding proteins may be used in conjunction for the design of an affinity chromatography step (see, e.g., Boraston et al., 2001).

In an example of prior art (U.S. Pat. No. 6,331,416) Shani et al. describe a method of expressing a recombinant protein with a polysaccharide binding domain that binds to the poorly defined cellulose in the host plant cell walls, and a protein purification process utilizing the affinity of this protein to host plant cellulose, resulting in a cell wall-protein complex that can be separated from soluble contaminating proteins. The strength of binding can be such that releasing the protein from the cellulosic host plant matter may require drastic conditions that denature the protein, having negative effects on the activity of the recombinant proteins being purified. Thus, although presenting a way to purify proteins from plant material the harsh conditions required for disrupting the ligand/cell-wall binding involve complications and concerns comparable to those mentioned above for antibody-Protein A elution.

To enable the use of affinity-based chromatography for large scale purification from plants, it is highly desirable to develop a non-denaturing protein purification process that is simpler and more economic than the current measures commercially available, with less coupling chemistry involved and compatible with the quality requirements of the pharmaceutical industry standards.

The carbohydrate binding domain CBM9-2 is from the *Thermotoga maritima* Xylanase 10A (Winterhalter et al 1995: Mol. Microbiol. 15 (3), 431-444). The CBM9-2 genomic DNA sequence is available as GenBank Accession No. Z46264 and it belongs to the Family IX of CBM-s and has number of attractive properties for high-resolution affinity purification, including non-denaturing eluting conditions using 1M glucose as a eluent, and high specific affinity for amorphous as well as crystalline celluloses (Boraston et al. 2001: Biochemistry 40, 6240-6247).

Recovery and purification of expressed recombinant proteins from transgenic plants is probably the most critical factor in establishing plants as a practical alternative system for protein production. It is essential that the number of processing steps be minimized and that each step be carried out at much higher efficiencies. (Moloney 2000)

This emphasizes a recognized need for a downstream process for purification of heterologous proteins from transgenic plant material that is efficient, simple, and economical. Furthermore, there is a need for such a downstream process consisting of gentle, non-denaturing conditions for the protein of interest, (in particular, specific affinity purification methods with gentle elution conditions) in order to secure bioactivity of the protein of interest, and improve yields.

A non-denaturing protein purification process free from the limitations detailed above could significantly lower the production cost involved in the production of biopharmaceuticals from plants, and would be enabling for the purification of heterologous proteins of value for which downstream processing has been prohibitively complex and costly.

SUMMARY AND OBJECTS OF THE INVENTION

The primary objective of present invention is to provide an improved, non-denaturing method for protein purification of high-value heterologous proteins produced in plants, plant derived tissue or plant cells.

The invention aims to reduce the cost and improve the quality of downstream processing of heterologous proteins produced in plants.

An important step in the purification process is the separation of the protein of interest as a CBM-fusion protein from cell-wall fragments and other poorly defined plant-derived solids as the CBM-fusion protein of the invention does not bind to these components. This can be done separately prior to an affinity chromatography step or simultaneously with an affinity chromatography step.

In a first aspect, the invention provides a non-denaturing method for production and purification of a soluble heterologous fusion protein comprising a cellulose binding module (CBM), from transgenic plants or transgenic plant cells expressing said fusion protein, the method comprising:

disrupting the transgenic plant material;

adding an extraction liquid to the plant material, thereby creating a mixture of soluble and insoluble plant material, so as to extract the soluble fusion protein from said disrupted plant material to the liquid phase to obtain a protein extract;

separating the insoluble plant material, comprising cell-wall material and solids, from said protein extract comprising said fusion protein of interest;

contacting said protein extract to a polysaccharide matrix which binds to said fusion protein;

washing the matrix with the bound fusion protein with one or more suitable aqueous solutions such as one or more buffer solutions, i.e., the washing may be preformed in one step, with a gradient or as a sequence of different washing solutions; and eluting the fusion protein from said polysaccharide matrix by adjusting conditions effecting the release of said fusion protein from the matrix under characteristically mild conditions.

Typically, the transgenic plant or plant cell is selected from the group of dicotyledonous plants and monocotyledonous plants, and in preferred embodiments said plant cell or transgenic plant is from the group of tobacco, rape seed, soy bean, lettuce, alfalfa, barley, maize, wheat, oat and rice.

The separation step comprises in some embodiments a method selected from expanded bed adsorption (EBA), packed mode chromatography, precipitation, filtration, centrifugation, or any combination thereof.

The affinity binding step binding the fusion protein to a polysaccharide matrix preferably comprises a chromatography step.

However, in certain useful embodiments, said separation of cell-wall fragments and other poorly defined plant-derived solids from the protein of interest—the CBM-fusion protein, and the affinity binding of the CBM fusion protein to a polysaccharide matrix can be done in a single powerful purification step using Expanded Bed Adsorption chromatography (EBA) with a suitable, inexpensive polysaccharide matrix. This feature streamlines and improves the economy of the downstream processing.

In advantageous embodiments of the present invention, the polysaccharide matrix comprises cellulose, and preferably pharmaceutically compatible cellulose. Such a well-defined pharmaceutical grade cellulosic matrix to which the CBM-fusion protein binds allows various high-end uses of the purified heterologous protein. A useful pharmaceutically compatible cellulose material for use as the polysaccharide matrix comprises Avicel™ (FMC Corporation, PA, USA).

The polysaccharide matrix used for affinity chromatography according to the invention requires no complex coupling chemistry or immobilization of potentially leaching ligands. The polysaccharide matrix provides both structural support and rigidity while constituting the affinity adsorbent itself. Thereby, more economical and safer protein purification is enabled for plant derived heterologous proteins.

It is still an advantage of this invention that the process described is amenable for different polysaccharide matrices of differing qualities all according to the different end-use of the purified heterologous proteins e.g. in for example agriculture, chemical industry or pharmaceutical industry. An affinity adsorbent made out of polysaccharide of pharmaceutical grade is a bulk material within the pharmaceutical industry and is considerably less expensive than any commercially available affinity chromatography media. Thus, an affinity matrix of very high quality can be made economical using the process described by this invention, enabling more economical downstream processing of high-value proteins from plant derived material.

It is a further advantage of the present invention that once the plant derived CBM-fusion protein is bound to the polysaccharide chromatography matrix, and after washing the matrix to remove any contaminating endogenous plant proteins, the fusion protein can be eluted from the column using nondenaturing, mild conditions typically under neutral or acidic conditions and preferably with the addition of soluble carbohydrates (sugars), that preserve the activity and structure of any fusion partner protein attached to CBM. The sugars compete with cellulose for the binding site of the CBM and a suitable concentration will release substantially all of the bound CBM fusion protein.

It follows that the preferred CBM-s that are used in the methods of the invention and fused to the heterologous protein of interest are such CBM-s that have desired binding characteristics to allow sufficiently strong binding to a suitable polysaccharide matrix to obtain a high yield of bound CBM fusion protein, and releasing by such mild conditions as described above. CBM9-2 has been found to have these desired characteristics. The use of other CBM-s with such characteristics is also within the scope of the invention. Such CBM-s may be found e.g. by searching available gene databases for sequences encoding CBM having desired characteristics, e.g. sequence motifs found to be similar to motifs in CBM9-2 that are important for the, binding characteristics.

Also, existing CBM-s may be modified with point mutation techniques well known in the art to modify their binding characteristics in order to obtain suitable CBM-s according to the invention.

After the fusion protein has been eluted from the polysaccharide affinity matrix it may optionally be subjected to one or more further purification or isolation steps, depending on the desired form and use of the protein.

In useful embodiments, the transgenic plant or plant cell comprises a nucleic acid sequence encoding for a CBM, preferably the CBM is heat-stable and remains soluble at elevated temperatures. The term heat-stable in this context indicates that the protein remains soluble, correctly folded and active at elevated temperatures, i.e. temperatures above about 25° C., and typically above about 37° C., including the range of 40° C.-100° C.

Genes encoding such preferred CBM may be obtained from thermophilic organisms, including thermophilic bacteria, algae and fungus and introduced into the host plant or plant cell in such a way as to express a fusion protein comprising said CBM. The term thermophilic refers herein to organisms with optimal growth temperature over 40° C. A preferred CBM is coded for by the xylanase 10A gene from *Thermotoga maritima*, preferably the region within the host plant or plant cell that codes for a CBM is a region of said gene. Said region coding for a CBM may in certain embodiments comprise a sequence depicted as SEQ ID NO: 1, or a nucleic acid sequence encoding the same amino acid sequence, or a sequence encoding an amino acid sequence with substantial sequence identity to said amino acid sequence.

It may be useful in some embodiments of the invention to heat the protein extract comprising the soluble fusion protein, such as to a temperature in the range of 37° C. and 100° C., e.g. a temperature in the range of 50-80° C., for a period of time such as in the range of from 1 min to 120 minutes during the process. For this purpose, heat-stable CBM such as from thermophilic sources is particularly useful. In some useful embodiments, the heat-stable CBM may promote solubility of attached heterologous protein at elevated temperatures, a feature that may be used for CBM-fusion protein enrichment of an extract containing other heat labile plant proteins. During such heating, a part of the endogenous plant proteins may become inactivated and/or denatured and may thus readily be separated from the protein extract. Said heated extract may preferably be subjected to the process step comprising expanded bed adsorption with a polysaccharide matrix for the simultaneous separation of solids and affinity binding of said CBM fusion protein from the heated extract.

In a highly useful embodiment of the invention, said fusion protein comprises a CBM and a heterologous polypeptide of interest intercepted by a stretch of amino acids comprising a proteolytic cleavage site, preferably a proteolytic cleavage site recognized and cleaved by a specific protease. By having such a site, the CBM can readily be cleaved off the fusion partner in the fusion protein to obtain the desired purified heterologous protein without the accompanying CBM. Detailed description for such successful purification involving a specific protease is disclosed in applicant's co-pending application "A process for proteolytic cleavage and purification of recombinant proteins" which application is filed simultaneously with this application and is incorporated herein in full by reference.

The present invention successfully addresses the shortcomings of downstream processing involved in of heterologous protein production at large scale, for purposes such as, but not limited to, agriculture, chemical industry and the production of protein-based pharmaceuticals. In particular, it provides a novel process of separating CBM-fusion proteins from biomass such as plant-derived cellulosic material, with fewer processing steps involved, taking advantage of a safer and more economical affinity chromatography principle amenable for use within the pharmaceutical industry, gentle elution conditions maintaining the activity of high-value heterologous proteins, and in applicant's co-pending application "A process for proteolytic cleavage and purification of recombinant proteins" comprising a process step enabling the recycling of a specific high-value protease in the process.

DETAILED DESCRIPTION OF PRESENT INVENTION

Herein below, the present invention will be described in more detail. Unless defined otherwise, all technical and scientific terms used herein have the same meaning as is commonly understood and used by one of skill in the art to which this invention belongs.

The term "polypeptide" used herein refers to any polymer of amino acids, being monomeric or multimeric, and does not refer to a specific length of a polymer of amino acids. Thus, for example, the terms peptide, oligopeptide, protein, and enzyme are included within the definition of polypeptide. This term also includes polypeptides with post-expression modifications such as for example, glycosylations, acetylations, phosphorylations and the like.

The term "heterologous polypeptide of interest" or "polypeptide of interest" used herein refers to any polypeptide intended for expression in plant-cells or plant tissue using the methods or compositions of the present invention. As non-limiting examples, pharmacological polypeptides (e.g., for medical uses) or industrial polypeptides (e.g. enzymes) can be produced according to the present invention.

The term "downstream processing" refers to the isolation and purification of a biotechnological product to a form suitable for its intended use.

The term "fusion partner" refers herein to a heterologous protein linked to CBM.

Figure 5:
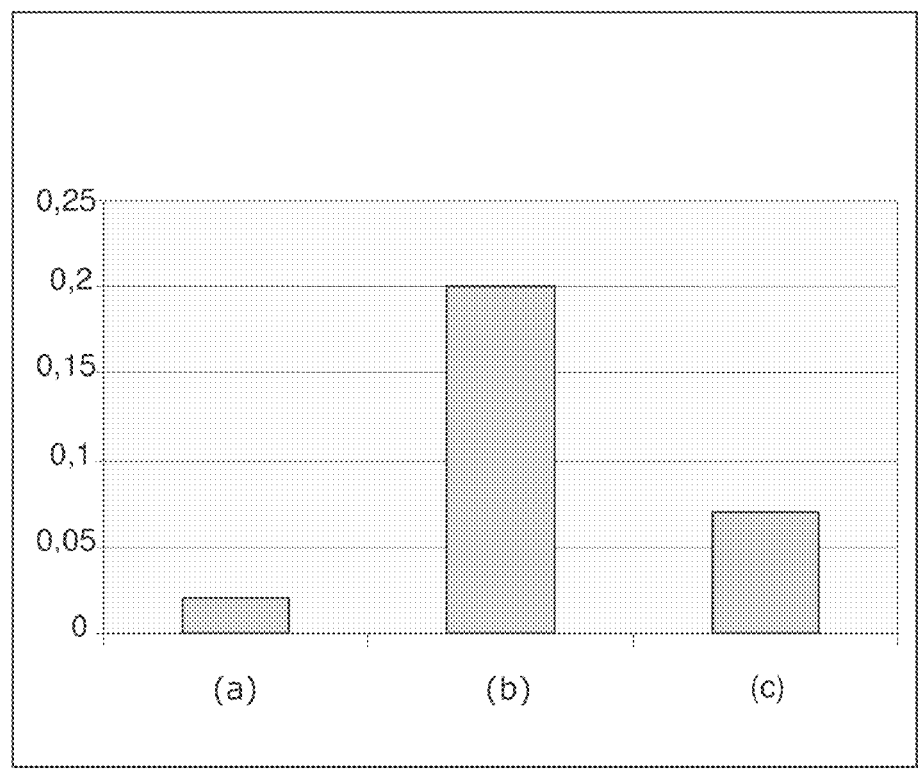
FIG. 5 demonstrates results obtained from Example 4. The graph shows ELISA readings of a control sample and a minimal reading of sample containing a heterologous protein of interest (HoxB4) fused to CBM9-2 and purified according to the down-scaled version of the purification process described herein. The columns show the measured ELISA values for (a) elution buffer, (b) fusion protein extracted from transgenic seeds, and (c) protein extracted from non-transgenic seeds.

FIG. 5 demonstrates results obtained from Example 4. The graph shows ELISA readings of a control sample and a minimal reading of sample containing a heterologous protein of interest (HoxB4) fused to CBM9-2 and purified according to the down-scaled version of the purification process described herein. The columns show the measured ELISA values for (a) elution buffer, (b) fusion protein extracted from transgenic seeds, and (c) protein extracted from non-transgenic seeds.

DETAILED DESCRIPTION OF PRESENT INVENTION

Herein below, the present invention will be described in more detail.

Unless defined otherwise, all technical and scientific terms used herein have the same meaning as is commonly understood and used by one of skill in the art to which this invention belongs.

The term "polypeptide" used herein refers to any polymer of amino acids, being monomeric or multimeric, and does not refer to a specific length of a polymer of amino acids. Thus, for example, the terms peptide, oligopeptide, protein, and enzyme are included within the definition of polypeptide. This term also includes polypeptides with post-expression modifications such as for example, glycosylations, acetylations, phosphorylations and the like.

The term "heterologous polypeptide of interest" or "polypeptide of interest" used herein refers to any polypeptide intended for expression in plant-cells or plant tissue using the methods or compositions of the present invention. As non-limiting examples, pharmacological polypeptides (e.g., for medical uses) or industrial polypeptides (e.g. enzymes) can be produced according to the present invention.

The term "downstream processing" refers to the isolation and purification of a biotechnological product to a form suitable for its intended use.

The term "fusion partner" refers herein to a heterologous protein linked to CBM.

The term "CBM fusion protein" refers to a molecule consisting of a CBM linked to a heterologous protein, and in the context it is put forward in this invention, a molecule without a proteolytic cleavage site, unless described otherwise.

The term "operably linked" refers to a functional linkage between a promoter (nucleic acid expression control sequence, or array of transcription factor binding sites) and a second nucleic acid sequence, wherein the promoter directs transcription of the nucleic acid corresponding to the second sequence.

The term "denatured" refers to a condition of a protein where the native structure, and consequently the activity of the protein is disrupted, and the protein is unfolded or incorrectly folded changing its native three-dimensional structure.

The term "expression" and "production" refer to the biosynthesis of a gene product, including the transcription and translation of said gene product.

"Molecular farming" refers to the operation of using plants of any kind in open fields or in closed facility to express and produce heterologous proteins in their tissue The term "transgenic" refers to a any cell, cell line, tissue plant part, organ or organism into which a non-native nucleic acid sequence has been introduced, and therefore altering its genotype, as is progeny thereof in which the non-native nucleic acid is present. Typically, the non-native nucleic acid sequence was introduced into the genotype by a process of genetic engineering, or was introduced into the genotype of a parent cell or plant by such a process and is subsequently transferred to later generations by sexual crosses or asexual propagation.

"Substantial sequence identity" indicates in the context herein at least 50% sequence identity and more preferably at least 60% such at least 70 sequence identity, such as at least 80% and preferably at least 90% sequence identity, such as at least 95% or 99% sequence identity. Algorithms for sequence analysis are known in the art, such as BLAST, described in Altschul et al., *J. Mol. Biol.* (1990) 215:403-10. Generally, the default settings with respect to, e.g. "scoring matrix" and "gap penalty" will be used for alignment.

The term "transformation" or "transformed" refers to the introduction of a nucleic acid sequence into the DNA genome of a host organism, irrespective of the techniques used for the introduction of the nucleic acid fragment into the host cell.

"Thermophilic" refers to an organism with optimal growth temperature over 45° C.

The term "GMP" (good manufacturing practice) dictates the manner in which biopharmaceuticals and other drugs and medical devices are produced. GMP requirements include standard operating procedures, sterile conditions, validation of materials and equipment and trained personnel.

Monocotyledonous and dicotyledonous plants that can be genetically manipulated can be used in the present invention. Preferably the plant is a monocotyledonous, more preferably barley, and most preferably the barley *Hordeum vulgaris*. A plant that can be genetically transformed is a plant into which non-native DNA sequence, including DNA sequence for a coding region, can be introduced, expressed, stably maintained, and transmitted to subsequent generations of progeny. Genetic manipulation and transformation methods have been used to produce barley plants that are using herbicides including, for instance, bialaphos or basta, or antibiotic, such as hygromycin, as selectable markers.

Methods

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Although only preferred embodiments of the invention are specifically illustrated, numerous modifications and variations in the invention as described in the above examples are expected to occur to those skilled in the art, without departing from the spirit and intended scope of the invention.

Figure 1:
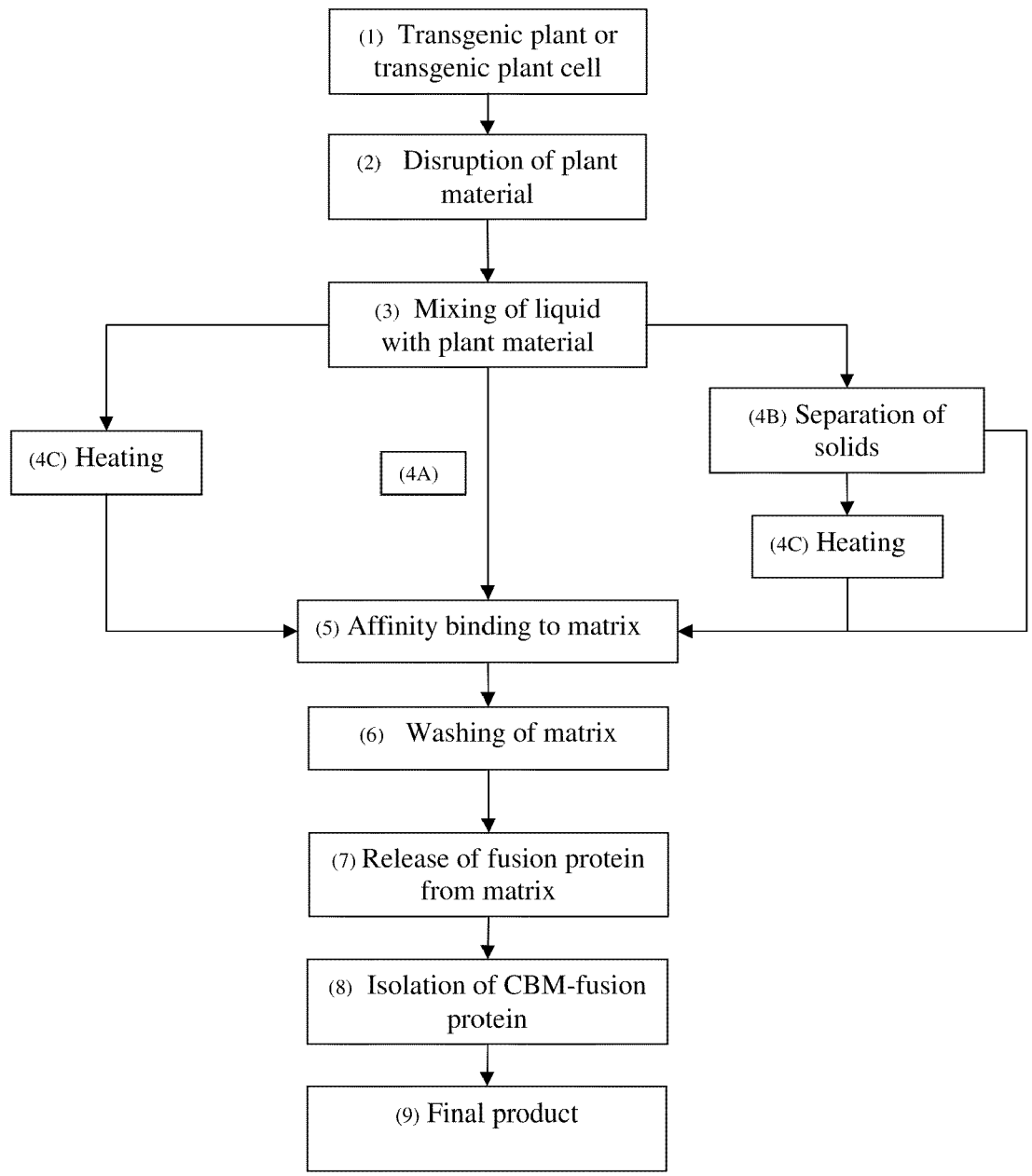
FIG. 1 is a schematic diagram of a preferred embodiment of the purification process.

Referring to FIG. 1 illustrating a schematic diagram of the purification process the process can be described as follows:

(1) The starting material for the process is a transgenic plant, material derived from transgenic plants or transgenic plant cells, including, but not limited to, suspension cultures of plant cells as well as undifferentiated cells of calluses. The material is transgenic in a way that it expresses in a controlled manner a heterologous gene(s) operably linked to a CBM open reading frame, that have been introduced to the plant cells through processes known to a person skilled in the art, such as, but not limited to, *Agrobacterium*-mediated transformation or particle bombardment-mediated transformation or plant viral vector-mediated transformation. The starting material is preferably selected on the basis of satisfactory expression levels of the fusion protein, as deemed by an analysis of RNA or protein levels by a person skilled in the art, prior to the initiation of the process described by the invention.

(2) Disruption of the transgenic material is accomplished by any method known to a person skilled in the art, that results in homogenization of the plant tissue and plant cells, in a dry or wetted state. A variety of methods can be chosen from, that suit the source of the plant material. Thus, for seeds, milling is a good way of disrupting the transgenic plant tissue, while for leaves and softer green tissue homogenizing can be accomplished with equipment such as, but not limited to, Waring blender, Sorvall Omnimixer or Polytron homogenizers. The equipment for disruption of plant tissue and plant cells is commercially available and easy to scale up as required. General methods of extraction of proteins from plant sources are described by G. Paul Powell in a publication edited by S. Roe, Protein purification applications, 2nd edition (2001). A simple and successful method of extraction of soluble proteins from plant sources is the addition of simple buffers like Low salt buffer to the disrupted, homogenized plant tissue, with thorough mixing. Precautions against oxidative tanning, such as addition of polyvinyl pyrrolidine (1% w/v) are usually sufficient to optimize purification from most plant tissues in order to sequester phenolics from the plant tissue that otherwise could have negative effects on the heterologous protein to be purified. Proteolysis does not always cause problems with plant sources. If, however, proteolysis is a concern, protease inhibitors, such as, e.g., serine-, cysteine- and metalloprotease inhibitors can be added to the extraction buffer. The disruption of the plant material can be done in the presence or absence of a buffered solution. The extraction solution may or may not contain reducing agents such as, but not limited to 2-mercaptoethanol or dithiothreitol (DTT). Soluble plant proteins will be present in the liquid phase together with the CBM-fusion proteins (3) Mixing of liquid with plant material is essential to extract the water-soluble fusion protein to the liquid phase. The liquid added may or may not contain buffering agents to control pH, preferably within the range of about 5.2 to 8.3, it may or may not contain any reducing agents or sequestering agents as described in (2) accordingly to the protein of interest. In its simplest form, the liquid can be water. After thorough mixing of liquid with the disrupted and homogenized plant material, the liquid phase now contains the CBM-fusion protein.

(4) (A) Depending to some degree on the level of homogenization the mixture of disrupted plant material and extraction liquid can be applied directly to an Expanded Bed Adsorption (EBA) column. In this approach the mixture is applied to the column as a stream of fluid through an expanded bed of affinity adsorption matrix of polysaccharide nature. During the streaming through the column the fusion protein in the liquid phase is exposed to the polysaccharide matrix and is selectively adsorbed through the selective affinity of the CBM to the polysaccharide adsorbent media. Particles such as, but not limited to, cell wall fragments and other solids, together with any soluble plant proteins are flushed through the EBA column in the flow-through liquid.

4(B) Alternatively, a majority of the solids in the mixture can be separated from the liquid prior to the affinity binding step through a variety of methods known to a person skilled in the art, these include, but are not limited to, precipitation, filtration, centrifugation, and sedimentation. As described hereinabove, the solids are discarded and the liquid containing the CBM-fusion protein is subjected to an optional heating step 4(C) or applied directly to the affinity binding step (5).

4(C) Heating of the mixture or liquid prior to affinity step (5) is optional, but may act as an additional purifying step in cases where the CBM-fusion protein as a whole remains soluble at elevated temperatures, while soluble plant proteins may denature and precipitate and endogenous plant proteases may be inactivated through heat. For this purpose, the heating procedure, taking into account the nature of the CBM-fusion protein, may involve heating in the range of 50° C. to 100° C., for a period of time in the range of 2 min to 60 minutes during the process. In these embodiments CBM of thermophilic origin are particularly beneficial.

(5) Affinity binding to matrix. The liquid protein extract containing the plant derived CBM-fusion protein is brought into contact with the polysaccharide matrix towards which the CBM has affinity for. The contact can be effected in various ways, such as, but not limited to, chromatography columns packed with the polysaccharide matrix where the liquid is run through the column in either packed or expanded mode, referring to the density of the polysaccharide matrix, or it can be effected in batch mode where the polysaccharide matrix is mixed together with the liquid in a suitable container, with the subsequent recovery of the matrix and the adsorbed CBM-fusion protein. The polysaccharide matrix can be of cellulosic origin such as, but not limited to, Avicel, or it can be of xylanoic origin, such as insoluble xylan. The binding specificity and thermodynamics of CBM9-2 have been studied in detail in a recent publication by Boraston et. al. (2001). It has however surprisingly been found by the present inventors, in contrast to what is indicated in the prior art, that following the methods of the present invention as described herein, CBM9-2 does not bind to plant cell wall components but becomes readily soluble, while retaining good specific binding to a polysaccharide matrix such as used in the affinity adsorption step herein (5). As described herein above this surprising quality introduces several advantages to downstream processing of plant derived CBM-fusion proteins to the extent that a greatly improved downstream processing method is provided.

(6) Washing of the matrix. The polysaccharide affinity adsorbent with CBM-fusion protein bound to it can be washed with several column volumes (relevant quantitative term if the affinity matrix is placed in a chromatography column) of an aqueous solution (e.g., water) or buffer, such as, but not limited to phosphate buffered saline or Tris-based buffers. To improve the efficiency of the washing step, the composition of the washing buffer may be adjusted by means such as, but not limited to, several column volumes of stepwise changes or a gradient of salt concentration or detergent, used to release weakly but nonspecifically bound contaminating proteins from the matrix.

(7) Release of fusion protein from matrix. By using CBM-s with the desired binding characteristics as described herein, elution of the CBM-fusion protein from the affinity matrix can be effected with the exposure of the CBM-fusion protein to competing saccharides such as, but not limited to glucose, galactose, lactose, maltose, and cellobiose. Any of these or other similar saccharides, or a combination thereof, can be added in a suitable amount, such as in the range of 1 mM to 1 M concentration to an elution buffer such as, e.g., phosphate buffered saline or Tris-based buffers, for the elution step. The saccharide concentration can be e.g. in the range 25 mM to 1 M, such as in the range 50-500 mM. These saccharides are commercially available as low-cost bulk chemicals, further improving the overall economy of the downstream processing according to the invention.

(8) Isolation/purification of fusion protein. Further purification/isolation of the CBM-fusion protein may be advantageous or required be in some instances. Such further isolation can be accomplished with any of the commonly available chromatographic procedures known to a person skilled in the art, such as, but not limited to, ion exchange chromatography or size exclusion chromatography.

(9) Final product. The final product is in this case a CBM-fusion protein in a highly purified form, ready for optional proteolytic cleavage of the CBM-fusion protein or further purification/isolation that may be required or be advantageous in some instances. This further isolation can be a chromatography step, such as, e.g., ion exchange chromatography or size exclusion chromatography.

The highly purified form is ready for further formulation and packaging in its final form, if necessary.

Additional objects, advantages, and novel features of the present invention will become apparent to one ordinarily skilled in the art upon examination of the following examples, which is not intended to be limiting. Additionally, each of the various embodiments and aspects of the present invention as delineated hereinabove and as claimed in the claims section below finds experimental support in the following examples.

EXAMPLES

Example 1

Biomass Interaction Study: CBM9-2 and Milled Barley Seed

Dried barley seed was finely ground in a Retsch mill to a fine flour. 1 g of milled seed was used for the extraction of water-soluble components from the seed with 5 ml of low salt buffer (50 mM potassium phosphate buffer pH 7.02), as a means to rid the sample of all water-soluble components that might interfere with the biomass interaction study. The mixture was vortexed and tumbled for 5 minutes to ensure thorough mixing of the liquid and the milled barley seed material. Following this mixing, the samples were centrifuged at 5000×g for 4 minutes to pellet the solids. After centrifugation, the supernatant was discarded. This procedure was repeated 3 times with low salt buffer, with the supernatant discarded after each centrifugation. Then the washing procedure was repeated 3 times with high salt buffer (50 mM potassium phosphate buffer pH 7.02, 1 M NaCl), the supernatant discarded as before. The resulting washed solids representing for the most part plant cell-wall fragments and insoluble starch. The washed solids were equilibrated with 3 times washing with low salt buffer as described above, to obtain same conditions that favor affinity binding of CBM9-2 to cellulosic matrix in affinity chromatography. A representative sample of the solids before biomass interaction study was taken for SDS-PAGE analysis (lane 3). 10 µl of bacterially produced CBM9-2 purified on cellulose (Avicel™)-affinity column (O.D. @280 nm 0.394), were taken for later SDS-PAGE (lane 2). The purified CBM9-2 had previously been subjected to repeated (4×) dilution and concentration in a ultrafiltration module as a proven method for desorbing any bound glucose from the CBM9-2, so as to regain the cellulose binding affinity characteristic of the protein.

Figure 2:
FIG. 2 demonstrates the results obtained from Example 1 by SDS-PAGE analysis. Lane 1: molecular weight size markers, lane 2: purified CBM9-2, lane 3: washed solids from milled barley seed, lane 4: supernatant after biomass interaction, lane 5: first wash with low salt buffer, lane 6: fifth wash with high salt buffer.

2 ml of the purified CBM9-2 were added to the washed, equilibrated solids derived from milled barley seed and the mixture incubated while shaking for 60 minutes at room temperature. After incubation, the mixture was spun down at 5000×g for 10 minutes, and the supernatant subsequently clarified with centrifugation at 13.000×g for 5 minutes. 10 µl of the clarified supernatant from the biomass interaction was taken for SDS-PAGE analysis (lane 4). Subsequently the pellet consisting of the milled barley seed solids, was washed 5 times with low salt buffer and subsequently 5 times with high salt buffer as described above. 10 µl of the first low salt buffer wash (lane 5) and the fifth low salt buffer wash (lane 6), were prepared for subsequent SDS-PAGE analysis. To elute any bound CBM9-2 from the milled barley seed solids, 1 ml of elution buffer (1 M glucose in 50 mM $KPO_4$, pH 7.02) was added to the solids and incubated during mixing for 15 minutes, before centrifugation at 5000×g for 5 minutes and removal of the supernatant (eluate). A 10 µl sample of the eluate was prepared for SDS-PAGE analysis (lane 7). A representative sample from the solids after the biomass interaction study and elution was taken for SDS-PAGE analysis (lane 8). The samples from the biomass interaction assay prepared for SDS-PAGE were run on 12.5% SDS-PAGE gels (PhastGels homogenous 12,5) using PhastSystem (Amersham Pharmacia Biotech). After completion of the run the gel was stained with Coomassie Blue R-250, and destained. The results are illustrated in FIG. 2.

These results demonstrate that CBM9-2 does not bind significantly to plant derived cell-wall fragments or other insoluble solids from milled barley seed.

Example 2

Purification of CBM9-2 from Milled Barley Seed Extract

Figure 3:
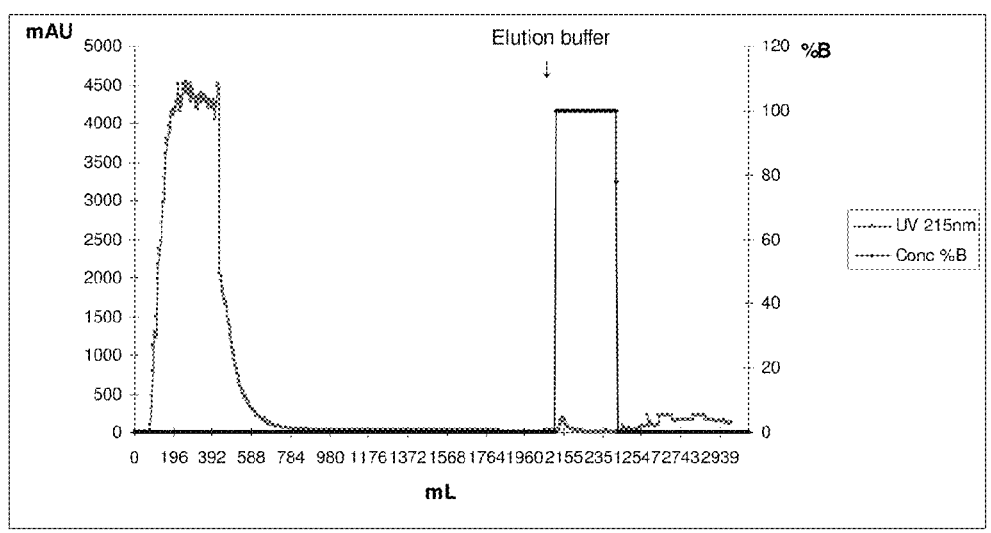
FIG. 3 demonstrates the successful purification of CBM9-2 from milled barley seed extract according to the method of this invention, as described in detail in Example 2. The figure shows the chromatographic profile of an expanded bed absorption (EBA) column with 200 mL cellulose.

Barley seeds were milled to finely ground flour using commercially available mill (Aarslev Maskinfabrik, Erhvervsvangen 11, 5792 Aarslev, D K). The resulting barley flour was wetted in Low salt buffer (50 mM potassium phosphate buffer pH 7.02) in volume-ratios 2:3, barley flour:buffer, respectively. The liquid was mixed thoroughly with the flour in a vessel and allowed to sediment overnight at 4° C. CBM9-2 purified from bacteria was added to the barley seed-supernatant. The next day the spiked supernatant (100 ml) containing CBM9-2 was fed to a Streamline 25 (Amersham Biotech) chromatography column containing cellulose (Avicel™). The feed application was done at flowrate 184 cm/h, in expanded bed mode, followed by a washing step with 5 column volumes high salt buffer (1 M NaCl in 50 mM $KPO_4$, pH 7.02), followed by 5 column volumes of low salt buffer (50 mM $KPO_4$, pH 7.02). The expanded column bed was allowed to sediment (sedimented bed height=20 cm) and elution was performed at 92 cm/h with 300 ml of elution buffer: 1 M glucose in 50 mM $KPO_4$, pH 7.02). The elution conditions resulted in a small peak containing the CBM9-2 protein (see FIG. 3).

This showed that using the procedure described hereinabove that firstly; CBM9-2 remains in solution unattached to cell-wall fragments and other poorly defined solids from milled barley seed, secondly; it is possible to use polysaccharidic affinity chromatography as described by this invention to capture CBM 9-2 from milled barley-seed extract, thirdly; this can be done by using well defined pharmaceutical grade cellulose (Avicel) as a matrix, and fourthly; the affinity chromatography step can be done in expanded bed mode as described by the invention, fifthly; the CBM9-2 purified from barley seed-extract can be eluted of the matrix under gentle conditions avoiding any denaturing steps, as described by this invention. The very same conditions and procedure as described hereinabove, can be applied to purify CBM9-2-fusion proteins from transgenic milled seed. The polysaccharidic affinity chromatography described is also valid for the separation of protease-CBM and excised CBM from the protein of interest after a proteolytic cleavage reaction, as described by this invention.

Example 3

Heat Stability and Enrichment of CBM9-2 in Extracts.

Figure 4:
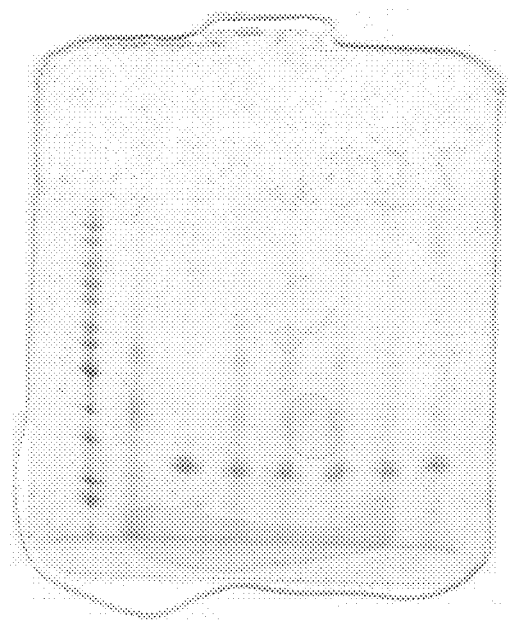
FIG. 4 demonstrates the results obtained from Example 3, Heat stability and enrichment of CBM9-2 in extracts. The figure shows a SDS-PAGE analysis of heat stability of CBM9-2 in barley extracts subjected to different temperatures. Lane 1: molecular weight size markers 10-200 kDa, lane 2: barley seed extract at room temperature (RT), lane 3: purified CBM9-2 (RT), lane 4: CBM9-2+barley seed extract (50° C.), lane 5: CBM9-2+barley seed extract (60° C.), lane 6: CBM9-2+barley seed extract (70° C.), lane 7: CBM9-2+barley seed extract (90° C.).

1.5 grams of milled barley were dissolved in 7.5 ml of Low salt buffer (50 mM $KPO_4$, pH 7.02). The solution was continuously mixed in a tumbler for 1 hr. And spun down at 6000 rpm for 10 minutes. The supernatant (extract) was measured for protein content with Bradford assay and found to contain 1.93 mg/ml of soluble seed proteins. 350 µl of extract were mixed with 350 µl of purified CBM9-2 protein (0.238 mg/ml) and aliquoted to Eppendorf tubes that were subsequently exposed to different temperatures (room temperature, 50° C., 60° C., 70° C. and 90° C.) in a water bath for 10 minutes. After heat treatment the samples were spun down at 11.000 rpm for 10 minutes and samples from the different heat treatments analysed by SDS-PAGE. The samples from the heat stability test were prepared for SDS-PAGE and run on 12.5% SDS-PAGE gels (PhastGels homogenous 12,5) using PhastSystem (Amersham Pharmacia Biotech). After completion of the run the gel was stained with Coomassie Blue R-250, and destained. The results are illustrated in FIG. 4. Further tests on the CBM9-2 exposed to heat confirmed that its ability to bind to cellulose was not adversely affected in anyway by the exposure to heat.

The results show that while soluble barley seed proteins were gradually lost from solution CBM9-2 remained soluble during the entire temperature range. This shows heat may be advantageously applied for the purpose of enrichment of CBM and CBM-fusion proteins during extraction stage of the purification process described by this present invention.

Example 4

Purification of Heterologous Protein Attached to CBM9-2 from Milled, Single Barley Seed Extract.

In a down-scaled version of the purification procedure described hereinabove, single seeds of transgenic barley plants expressing heterologous protein of at room temperature for a period in the range of 30 sek to 5 min. When blue color had developed, 100 µl of 0.2 M Sulfuric acid was added. The color turned yellow, and the absorbance was measured in a microplate reader at 450 nm.

Results from an ELISA analysis of a single seed extraction from indivual transgenic barley seed are shown in FIG. 5.

The ELISA analysis, previously shown to be specific for CBM9-2, shows firstly; that heterologous fusion protein accumulation in individual seeds can be achieved and verified; that the procedure described hereinabove works for the isolation of a heterologous fusionprotein with cleavage site, even at small scale, supporting the scaleability of the purification process; it shows that heterologous protein of interest attached to CBM9-2 is succesfully maintained in solution during extraction and not lost due to binding to poorly defined plant cell wall cellulose; it shows that the heterologous fusionprotein is not exposed to denaturation during the chromatography process, as it is recognized after elution by the specific antibodies without any renaturation steps being involved, emphasizing the advantage of the present invention to several other harsher affinity chromatography procedures, as discussed hereinabove; that the purification procedure described hereinabove is applicable to any heterologous fusion protein attached to CBM9-2.

Example 5

Purification and Activity Measurements of CBM-Protease

In order to produce a site-specific protease with a CBM9-2 tag attached to it the following procedure was followed:

Agrobacterium tumefaciens strain AGL0 was constructed to contain a binary plasmid carrying an expression construct composed of a constitutive promoter in front of enterokinase cDNA to which was attached cDNA corresponding to CBM9-2, a signal sequence for targeting to Endoplasmic reticulum (ER) and a retention signal to maintain the protein in the ER. This agrobacterium strain was grown in YEB media under selection conditions, first in 10 ml for 2 days at 28° C. up to O.D. 600 of 0.8. The small culture is diluted 1:50 to 500 ml culture containing 20 µM acetosyringone for 2-3 days at 28° C. and vigorous shaking up to O.D. 600 nm of 2.5. The bacteria was spun down at 6.000 rpm for 10 minutes and resuspended in MS-solution (containing 55 g/l sucrose) to OD600 2.5. Acetosyringone was added (10 mM), for final concentration of 200 uM. Bacterial suspension was then kept at room temperature for 1 hour and Tween-20 (10%) added, for final concentration of 0.005%.

For transient expression of CBM-protease in lettuce plants were submerged into a bowl containing the Agrobacterium bacterial suspension for 15 seconds. Subsequently the plants were placed in a vacuum chamber and 0.4 bar pressure was applied for 20 minutes, after which air inlet was opened to equalize pressure rapidly. The excess bacteria on leaf surface was washed off with successive dipping into bowls of tap water. The lettuce plants were placed in a growth chamber with 16 hrs day/8 hrs night light period at 22° C., for 4 days.

The plants were harvested by excising the leafy tissue and subsequently frozen and kept at 86° C. The plants were homogenized using mortar and liquid nitrogen until a very fine powder was obtained. The powdered lettuce leaf material was extracted by the addition of 1.2:1 (vol:vol) low-salt extraction buffer and lettuce powder respectively, and proteins extracted for 30 minutes with occasional mixing at room temperature.

The extract was subsequently centrifuged at 6000 rpm for 20 minutes to separate solid material and cell wall fragments from liquid phase. The supernatant was decanted and spun again as previously described. The clear supernatant was fed onto a packed bed column containing cellulosic matrix (Avicel™) as described hereinabove. The CBM-protease attached specifically to the cellulosic matrix and after washing the column with 5 column volumes of high salt and low salt washing buffers, respectively, the CBM-protease was eluted off the column under mild, non-denaturing conditions, i.e. with 1 M glucose solution in a single peak.

The peak was subsequently concentrated using Millipore concentrators (Ultrafree-15—Biomax-5).

Enterokinase activity is assayed using specific synthetic substrate according to a standard approach (Grant & Hermon-Taylor, 1979): Synthetic substrate: Gly-Asp-Asp-Asp-Asp-Lys-β-naphthylamide ($GD_4K$-na); Assay conditions 37° C. Reaction volume is 1.5 ml. The reaction mixture consists of: 25 µl 10 mM $GD_4K$-na (0.5 mM), 125 µl 100 mM Tris-HCl, pH 8.4 (25 mM), 50 µl 100% DMSO (10%), 50 µl 100 mM $CaCl_2$ (10 mM), (20-100) µl enterokinase, 250 µl distilled $H_2O$-(20-100) µl. The rate of β-naphthylamine formation was determined from the increment of fluorescence between $\lambda_{ex}$=337 nm and $\lambda_{em}$=420 nm. This was monitored continuously for 5 min.

The results from the activity measurements showed that CBM-enterokinase produced and purified as described, was active; Enterokinase activity was measured to be 442.7 cps/min/µg compared to blank 0.0001 cps/min/µg.

The example shows firstly; that a protease-CBM can be produced in plants, in this case transiently in lettuce, and that CBM-protease can be isolated and purified successfully using the purification procedure described hereinabove. It further shows that the CBM9-2 affinity tag of the fusion protein is fully functional; that the CBM-protease effectively to cellulosic matrix and it can be eluted off the matrix under the mild elution conditions described by the invention, and the eluted protease is shown to be fully active. The enzymatically active purified product provides in itself evidence for the non-denaturing properties of the purification process, as enzyme activity is particularly sensitive for partial or full denaturation, which easily results in loss of activity. This shows effectively that all components of the invention are functional and that their behaviour and performance is such that they can easily be applied in the manner described by the invention hereinabove, resulting in a process constituting a major improvement in specificity, economy and efficiency of downstream processing of heterologous proteins of any source.

REFERENCES

Altschul et al., J. Mol. Biol. (1990) 215:403-10.
Boraston et al. (2001) Biochemistry 40, pp. 6240-6247.
Contributors (2001) in "Recombinant Protein Drugs" Ed. P. Buckel—from series-Milestones in Drug Therapy, Birkhauser Verlag, Basel 2001.
Grant D. A., Hermon-Taylor J., Blochim. Blophys. Acta 567 (1979), 207-11.
Hammond (1999) in "Plant bioechnology; new products and applications" Eds. Hammond, McGarvey & Yusibov, Springer Verlag, N.Y. 1999.
HIC, RPC, IEX, Principles and Methods Series, nr. 18-1020-90, nr. 18-11134-16, nr. 18-1114-21(respectively)—Amersham Pharmacia Biotech.
Kalyanpur M. (2000) in "Downstream processing of proteins" Ed. M. A. Desai Humana Press N.J.
Moloney M. (2000) in "Seed technology and its biological basis" Ed. M. Black and J. D. Bewley, Sheffield Academic Press, UK.
Paul G. Paul Powell G. in Protein purification applications", Ed. by S. Roe, "2nd edition (2001).
R. K. Scopes R. K. (1993) in "Protein Purification: Principles and Practice" 3rd ed. Springer-Verlag N.Y.
Shani et al. US Pat. No. 6,331,416.
Winterhalter et. al. (1995) Mol. Microbiol. 15 (3), 431-444.

The invention claimed is:

1. A method for production and purification of a soluble heterologous fusion protein comprising a cellulose binding module (CBM), from transgenic plants or transgenic plant cells expressing said fusion protein, comprising
   (a) disrupting the transgenic plant material;
   (b) adding an extraction liquid to the plant material, thereby creating a mixture of soluble and insoluble plant material, so as to extract the soluble fusion protein from said disrupted plant material to the liquid phase to obtain a protein extract;
   (c) separating the insoluble plant material, comprising cell-wall material and solids, from said protein extract comprising said fusion protein of interest;
   (d) contacting said protein extract to a polysaccharide matrix which binds to said fusion protein;
   (e) washing the matrix with the bound fusion protein with one or more suitable aqueous solutions; and
   (f) eluting the fusion protein from said polysaccharide matrix by adjusting conditions effecting the release of said fusion protein from the matrix,
   thereby obtaining the soluble heterologous fusion protein.

2. The method of claim 1 wherein said transgenic plant or plant cell is selected from the group of dicotyledonous plants and monocotyledonous plants.

3. The method of claim 1 wherein said plant cell or transgenic plant is selected from the group of plants including tobacco, rape seed, soy bean, alfalfa, lettuce, barley, maize, wheat, oat and rice.

4. The method according to claim 1, wherein the separation step (c) is selected from one or more of the group consisting of expanded bed adsorption (EBA), precipitation, filtration and centrifugation.

5. The method of claim 1 wherein affinity binding to said polysaccharide matrix in step (d) comprises a chromatography step.

6. The method of claim 1, combining steps (c) and (d) in a process step comprising expanded bed adsorption with a polysaccharide matrix, as a measure for simultaneous separation of cell-wall material and solids from said protein extract and affinity binding of said CBM-fusion protein onto the polysaccharide matrix.

7. The method of claim 1, wherein said conditions effecting the elution of said fusion protein from the matrix are neutral or acidic conditions or involving exposure to carbohydrates, or any combination thereof.

8. The method of any one of claims 1, 5, and 6, wherein said polysaccharide matrix comprises cellulose.

9. The method of claim 8, wherein said cellulose matrix comprises a pharmaceutically compatible cellulose.

10. The method of claim 9, wherein said cellulose is a microcrystalline cellulose.

11. The method of claim 1, wherein said transgenic plant or plant cell comprises a nucleic acid sequence encoding for a CBM.

12. The method of claim 11, wherein said CBM is heat-stable and remains soluble at temperatures higher than 25° C.

13. The method of claim 12, wherein said nucleic acid sequence encoding for a CBM is a coding region of the xylanase10A gene from *Thermotoga maritima*.

14. The method of claim 13, wherein said coding region for a CBM comprises a sequence depicted in SEQ ID NO: 1, or a sequence encoding the same amino acid sequence or an amino acid sequence with substantial sequence identity to said sequence.

15. The method of claim 1, wherein said protein extract is heated to a temperature in the range of 37° C. and 100° C., for a period of time in the range of from 1 mm to 120 minutes during the process.

16. The method of claim 15, wherein said heated extract is subjected to the process step comprising expanded bed adsorption with a polysaccharide matrix for the simultaneous separation of solids and affinity binding of said CBM fusion protein from the heated extract.

17. The method of claim 1, wherein said heterologous fusion protein comprises a protease.

18. The method of claim 17, wherein said protease is mammalian enterokinase (EK) or an enterokinase active part thereof.

19. The method of claim 18, wherein said EK comprises a bovine EK catalytic domain (EKc).

20. The method of claim 19, wherein said bovine EKc is encoded by the nucleic acid sequence shown as SEQ ID NO: 2.

21. The method of claim 1, wherein said fusion protein comprises a CBM and a heterologous polypeptide of interest intercepted by a proteolytic cleavage site.

22. The method of claim 13, wherein said CBM is the carbohydrate binding domain CBM9-2.

* * * * *